United States Patent
Daly

(10) Patent No.: US 7,769,419 B2
(45) Date of Patent: Aug. 3, 2010

(54) OCULAR PROPERTY MEASURING APPARATUS AND METHOD THEREFOR

(75) Inventor: Daniel John Daly, Berkshire (GB)

(73) Assignee: Lein Applied Diagnostics Limited, Berkshire (GB)

( * ) Notice: Subject to any disclaimer, the term of this patent is extended or adjusted under 35 U.S.C. 154(b) by 1139 days.

(21) Appl. No.: 10/576,718

(22) PCT Filed: Oct. 20, 2004

(86) PCT No.: PCT/GB2004/004435
§ 371 (c)(1),
(2), (4) Date: Apr. 21, 2006

(87) PCT Pub. No.: WO2005/044099
PCT Pub. Date: May 19, 2005

(65) Prior Publication Data
US 2007/0078308 A1  Apr. 5, 2007

(30) Foreign Application Priority Data
Oct. 24, 2003  (GB) .................. 0324872.1

(51) Int. Cl.
*A61B 5/145* (2006.01)
(52) U.S. Cl. ...................... 600/318; 600/316
(58) Field of Classification Search ................. 600/316, 600/318, 319
See application file for complete search history.

(56) References Cited

U.S. PATENT DOCUMENTS 3,958,560 A  5/1976  March ........................ 600/319
3,963,019 A  6/1976  Quandt ....................... 600/319
4,014,321 A  3/1977  March ........................ 600/319
4,154,114 A  5/1979  Katz .......................... 73/629

(Continued)

FOREIGN PATENT DOCUMENTS

EP  0589191  8/1984

(Continued)

OTHER PUBLICATIONS

Anumula, H., Nezhuvingal, A., Li, Y., Cameron, B., "Development of a Non-invasive Corneal Birefringence Compensated Glucose Sensing Polarimeter", Proc. SPIE vol. 4958, p. 303-312, Advanced Biomedical and Clinical Diagnostic Systems, Jul. 2003.

(Continued)

*Primary Examiner*—Eric F Winakur
*Assistant Examiner*—Etsub D Berhanu
(74) *Attorney, Agent, or Firm*—Chapin IP Law, LLC

(57) ABSTRACT

A method and apparatus for measuring an apparent depth (1) of a section of an eye (30) are disclosed. Light is focused to a measurement location (15) proximate or within the eye. The measurement location is scanned through the section and upon passing through first and second refractive index interfaces defining the section, a respective reflected light signal is detected, from which apparent positions of the first and second interfaces may be derived. Preferably, a confocal scanning arrangement is employed. Preferably, the section is the aqueous humor (34) of the eye (30). From changes in its refractive index (n) corresponding changes in glucose concentration in the aqueous humor and, in turn, in the bloodstream of a patient may be derived, offering a non-invasive monitoring means for diabetic patients. The apparatus may be a hand-held device, employing microelectromechanical systems. The radius of curvature (R) of a curved section, such as a cornea (32) or ocular lens (36), may also be measured to determine refractive errors of the eye.

40 Claims, 7 Drawing Sheets

U.S. PATENT DOCUMENTS

| | | | |
|---|---|---|---|
| 4,407,008 A | 9/1983 | Schmidt | 348/79 |
| 4,750,830 A | 6/1988 | Lee | 351/211 |
| 4,806,004 A | 2/1989 | Wayland | 359/389 |
| 5,209,231 A | 5/1993 | Cote | 600/310 |
| 5,433,197 A | 7/1995 | Stark | 600/319 |
| 5,553,617 A | 9/1996 | Barkenhagen | 600/318 |
| 5,582,168 A | 12/1996 | Samuels | 600/407 |
| 5,785,651 A | 7/1998 | Kuhn | 600/310 |
| 5,820,557 A | 10/1998 | Hattori | 600/319 |
| 5,880,465 A | 3/1999 | Boettner | 250/234 |
| 5,961,449 A | 10/1999 | Toida | 600/319 |
| 6,066,847 A | 5/2000 | Rosenthal | 250/252.1 |
| 6,152,875 A | 11/2000 | Hakamata | 600/319 |
| 6,181,957 B1 | 1/2001 | Lambert | 600/319 |
| 6,187,599 B1 | 2/2001 | Asher | 436/531 |
| 6,188,477 B1 | 2/2001 | Pu | 356/491 |
| 6,226,089 B1 * | 5/2001 | Hakamata | 356/432 |
| 6,267,477 B1 | 7/2001 | Karpol | 351/221 |
| 6,382,794 B1 | 5/2002 | Lai | 351/212 |
| 6,424,850 B1 | 7/2002 | Lambert | 600/319 |
| 6,442,410 B1 | 8/2002 | Steffes | 600/319 |
| 6,574,501 B2 | 6/2003 | Lambert | 600/473 |
| 6,585,723 B1 | 7/2003 | Sumiya | 606/5 |
| 6,836,337 B2 | 12/2004 | Cornsweet | 356/517 |
| 6,853,854 B1 | 2/2005 | Proniewicz | 600/319 |
| 6,934,035 B2 | 8/2005 | Yang | 356/485 |
| 6,961,599 B2 | 11/2005 | Lambert | 600/318 |
| 2002/0171804 A1 | 11/2002 | Rathjen | 351/221 |
| 2003/0211625 A1 | 11/2003 | Cohan | 436/95 |
| 2003/0225321 A1 | 12/2003 | Cote | 600/318 |
| 2003/0233036 A1 | 12/2003 | Ansari | 600/316 |
| 2004/0080759 A1 | 4/2004 | Shaver | 356/609 |
| 2004/0087843 A1 | 5/2004 | Rice | 600/319 |
| 2004/0138539 A1 | 7/2004 | Jay | 600/322 |
| 2004/0152963 A1 | 8/2004 | March | 600/319 |
| 2004/0257585 A1 | 12/2004 | Cornsweet | 356/517 |
| 2004/0260159 A1 | 12/2004 | Gerlitz | 600/319 |

FOREIGN PATENT DOCUMENTS

| | | |
|---|---|---|
| GB | 2 144 537 | 3/1985 |
| WO | WO 93/07801 | 4/1993 |
| WO | WO 97/13448 | 4/1997 |
| WO | 97/30627 | 8/1997 |
| WO | WO 99/44496 | 9/1999 |
| WO | WO 00/60350 | 10/2000 |
| WO | WO 2004/034894 A1 | 4/2004 |
| WO | WO 2004/064628 | 8/2004 |
| WO | WO 2005/120334 | 12/2005 |

OTHER PUBLICATIONS

Arnold, M., "Noninvasive Laser Measurement of Blood Glucose in the Eye: A Bright idea or an Optical Illusion", Diabetes Technology and Therapeutics, vol. 1, No. 2, 1999.

Baba, J., Cameron, B., Cote, G., "Effect of temperature, pH, and corneal birefringence on polarimetric glucose monitoring in the eye", Journal of Biomedical Optics 7(3), 321-328 (Jul. 2002).

Baba, J., Cote, G., "Dual-detector polarimetry for Compensation of Motion Artifact in a Glucose Sensing System", Optical Diagnostics and Sensing of Biological Fluids and Glucose and Cholesterol Monitoring II, Proc. SPIE vol. 4624 (2002), pp. 76-80.

Bockle, S., Rovati, L., Ansari, R., "Polarimetric glucose sensing using the Brewster-reflection off the eye lens: theoretical analysis", Proceedings of SPIE—vol. 4624 Optical Diagnostics and Sensing of Biological Fluids and Glucose and Cholesterol Monitoring II, May 2002, pp. 160-164.

Borchert M, Storrie-Lombardi M, Lambert J "A non-invasive glucose monitor: preliminary results in rabbits" Diabetes Technology & Therapeutics 1999; 1: 145-151.

Cameron, B., Gorde, M., Satheesan, B., Cote, G., "The Use of Polarized Laser Light Through the Eye for Noninvasive Glucose Monitoring", Diabetes Technology and Therapeutics, vol. 1, No. 2, 1999.

Chou C, Lin P-K "Noninvasive glucose monitoring with optical heterodyne Technique" Diabetes Technology & Therapeutics 2000; 2: 45-47.

Cote, G., "Non-Invasive and Minimally Invasive Optical Monitoring Technologies", Symposium of Innovative Non- or Minimally Invasive Technologies for Monitoring Health and Nutritional Status in Mothers and Young Children, Aug. 2000, Children's Research Center, Baylor College of Medicine, Houston, TX.

Li, H., Petroll, W., Moller-Pederson, T., Maurer, J, Cavanagh, H., Jester, J., "Epithelial and Corneal Thickness Measurements by in vivo confocal microscopy through focusing (CMTF)", Current Eye Research; (16): 214-221, 1997.

Li, J., Jester, J., Cavanagh, H., Black, T., Petroll, W., "On-Line 3-Dimensional Confocal Imaging in Vivo", Investigative Ophthalmology and Visual Science, Sep. 2000, vol. 41, No. 10, pp. 2945-2953.

Liu, J., Bagherzadeh, M., Hitzenberger, C., Pircher, M., Zawadzki, R., Fercher, A., "Glucose dispersion measurement using white-light LCI", Coherence Domain Optical Methods and Optical Coherence Tomography in Biomedicine VII, Proceedings of the SPIE, vol. 4956, pp. 348-351 (2003).

March, W., "Analysis: A Noninvasive Ocular Glucose Sensor", Diabetes Technology & Therapeutics, Jun. 2001, vol. 3, No. 2: 209-210.

March, W., Ochsner, K., Horna, J., "Intraocular Lens Glucose Sensor", Diabetes Technology & Therapeutics, May 2000, vol. 2, No. 1: 27-30.

Masters, B. and Bohnke, M., "Three-Dimensional Confocal Microscopy of the Living Human Eye", Annu. Rev. Biomed. Eng. 2002, 4:69-91.

McLaren, J., Nau, C., Erie, J., Bourne, W., "Corneal Thickness Measurement by Confocal Microscopy, Ultrasound, and Scanning Slit Methods", American Journal of Ophthalmology, Jun. 2004, pp. 1011-1020.

Rawer, R., Stork, W., Kreiner, C., "Non-invasive polarimetric measurement of glucose concentration in the anterior chamber of the eye", Graefe's Arch Clin Exp Ophthalmol (2004) 242: 1017-1023.

Sebag, J., Ansari, R., Dunker, S., Suh, K., "Dynamic Light Scattering of Diabetic Vitreopathy", Diabetes Technology and Therapeutics, vol. 1, No. 2, 1999.

Steffes P "Laser-based measurement of glucose in the ocular aqueous humor: an efficacious portal for determination of serum glucose levels" Diabetes Technology & Therapeutics 1999; 1: 129-133.

Wicksted JP, Erckens RJ, Motamedi M, and March WF. "Raman spectroscopy studies of metabolic concentrations in aqueous solutions and aqueous humor specimens" Applied Spectroscopy 49:987-993, 1995.

* cited by examiner

OCULAR PROPERTY MEASURING APPARATUS AND METHOD THEREFOR

CROSS-REFERENCE TO RELATED APPLICATION

This Application is a Section 371 National Stage Application of International Application No. PCT/GB2004/004435, filed Oct. 20, 2004 and published as WO 2005/044099 on May 19, 2005, in English.

FIELD OF INVENTION

The present invention relates to an ocular property measuring apparatus and method, for application especially, but not exclusively, in the determination of blood glucose levels in animals.

BACKGROUND OF THE INVENTION

Diabetes is a major and rapidly growing problem: there are estimates that over 170 million people suffer from the disorder worldwide. In addition, studies have shown that the incidence of juvenile-onset, insulin-dependent diabetes has doubled over the last 15 years. There has also been a doubling in the number of children under the age of 5 suffering from diabetes in just 10 years.

The symptoms associated with diabetes can be severe. If the blood glucose level is not suitably controlled by the patient, the physical damage which may be caused includes blindness, heart disease and gangrene. As such, the mortality rate for diabetics is significantly higher than the rate for the average person.

A person's blood glucose concentration varies over a relatively short timescale, due to a number of factors, such as the length of time since the patient's last meal, the type of food ingested, the amount of exercise taken, and whether or not the patient is otherwise ill. As a result, diabetics usually need to test their glucose levels many times a day, in order to monitor and control their condition. The actual testing regime varies between patients and is individually prescribed by the doctor or diabetes educator of the patient.

The primary method used for testing blood glucose concentration involves the taking of a blood sample, which is then analysed. In this test, a patient's finger or arm is pricked with a small needle and the resulting drop of blood is placed on a test strip, for analysis in a hand-held meter. If the glucose concentration reading is above an acceptable level, insulin must be injected into the blood stream to bring the glucose concentration back within an acceptable range.

Because of the frequency of testing required to monitor the blood glucose concentration, the patient is normally expected to perform the tests throughout the day, drawing and analysing the blood sample himself. There are a number of problems experienced by patients with the above procedure. Firstly, the technique is invasive and therefore carries the risk of infection. Secondly, continual pricking of the fingers causes hard skin. Thirdly, the process is clearly not pain-free. Finally, there is a large, ongoing consumables cost associated with this method. As a result of these and other problems, certain sectors of the diabetic population do not test themselves as often as required. This is particularly the case for the elderly, who tend to lack the fine motor skills required; teenagers, who tend to find the whole procedure socially embarrassing; and children, who tend not to accept the discomfort associated with the process.

A number of non-invasive blood glucose concentration measuring techniques have been proposed to overcome these problems. One particular approach which has been suggested involves measuring the glucose concentration of the aqueous humor in the anterior chamber of the eye, since, while varying between individuals, there is a close correlation between this concentration and the blood glucose concentration. Measurement of the glucose concentration of the aqueous humor may be achieved by various means; for example, by polarimetry (e.g., U.S. Pat. No. 5,896,198); by Raman techniques (e.g., WO-A-00/02479); by spectrometry (e.g., U.S. Pat. No. 5,969,815); or by reflectometry (e.g., U.S. Pat. No. 6,236,089).

A desirable alternative approach to measuring the glucose concentration in the aqueous humor involves measuring the refractive index of the aqueous humor, since there is a strong correlation between the refractive index and the glucose concentration.

U.S. Pat. No. 3,963,019 discloses a method and apparatus, by which a beam of light is projected into and through the aqueous humor of a patient's eye. The angular displacement of light reflected from the iris and through the aqueous humor is proportional to the refractive index of the aqueous humor. Hence by measuring the angle of the reflected light, the glucose concentration of the aqueous humor may be found. In practice, this technique measures the combined optical properties of the aqueous humor and the cornea and it is not trivial to deconvolve the effect of each. In addition, changes to the cornea, for example, will reduce the accuracy of readings taken in this way.

U.S. Pat. No. 6,152,875 discloses a method and apparatus, by which the refractive index of the aqueous humor may be derived by measuring the intensity of light reflected from the eye. The intensities of reflected light from the air/cornea and cornea/aqueous humor interfaces are measured and compared to determined how much light is reflected from the cornea/aqueous humor interface relative to the cornea/air interface. It is assumed that the amount of light reflected from the air/cornea interface is constant, and that the amount of light reflected from the cornea/aqueous humor interface is related to the refractive index of the aqueous humor. There are a number of practical limitations to this technique. For example, any stray light or reflections from other surfaces will cause inaccuracies in measurements, so additional steps such as interferometry, frequency shift, or ultra-short pulses are required to achieve the required accuracy. Since the method relies on the measurement of the relative reflected intensities from two surfaces of the eye, further inaccuracies may be introduced because of diurnal variations in the shape of the cornea, changes in the refractive index of the tear film (itself affected by the blood glucose level) and variations in atmospheric conditions, such as temperature and pressure, which will alter the refractive index of the air.

WO-A-03/025562 discloses an interferometric technique for measuring the refractive index of the aqueous humor. In this technique, two beams of light are shone onto the iris in the eye, one beam having a plane wavefront and the other beam having a spherical wavefront. The two beams interfere where they coincide on the iris, to form a pattern of dark and light rings at a detector. Changes in the refractive index of the aqueous humor affect the phase difference between the interfering beams and therefore the spacing of the fringes. The refractive index may thus be determined by measuring the spacing of the fringes. One practical problem with this technique is that a laser is required. A further problem is that interferometry is very sensitive to vibrations, with the result that the apparatus effectively needs to be arranged on an optical bench. In particular, this technique would not be suitable for use with a hand-held meter. Furthermore, with this interferometric arrangement, it is not possible to distinguish between corneal changes and changes in the aqueous humor.

There is a need, therefore, for an apparatus and method which employs a non-invasive, optical technique for the reliable determination of changes in the refractive index of the aqueous humor in the anterior chamber of an eye. In particular, it would be desirable for measurements made by such apparatus and method to be used to derive the concentration of glucose in the aqueous humor and, in turn, the concentration of glucose in the blood of a patient. There is also a need for an apparatus and method which may be used to determine the concentrations of other compounds in the aqueous humor, including both naturally occurring and intentionally introduced chemicals, and which may be used to measure other properties of the eye, such as corneal thickness and surface curvature.

The present invention aims to address the above and other objectives by providing an improved technique for the measurement of properties of an eye.

SUMMARY OF THE INVENTION

According to a first aspect of the present invention, there is provided a method of measuring changes in an apparent depth of the anterior chamber of an eye, the anterior chamber being defined by a first interface between the cornea and the aqueous humor of the eye and a second interface between the aqueous humor and the ocular lens of the eye, the method comprising the steps of: a) focusing light to a measurement location proximate or within the eye; b) scanning the measurement location through the anterior chamber; c) detecting reflected light from the measurement location as the measurement location passes through the first and the second interfaces and generating a signal representative of the detected light; d) deriving from the signal apparent positions of the first and the second interfaces and, therefrom, the apparent depth of the anterior chamber; e) comparing the derived apparent depth with a previous reference measurement of the apparent depth, so as to determine a change in the refractive index of the aqueous humor; and f) calculating a measure of change in concentration of an analyte of interest in the aqueous humor from the determined change of refractive index.

When the measurement volume, or location, is scanned through a section of the eye, incident light is reflected as a local peak each time the measurement location passes through an interface between two media of different refractive index. By recording the signal generated by a detector on receipt of this reflected light, a reflected light intensity profile may be obtained. The signal is associated with the apparent position of the measurement location, either in time or space, so that the apparent depth of the section may be derived. The apparent depth will typically differ from the real, or physical, depth of the section by the refractive index of the section. Changes in the apparent depth may therefore be used to calculate changes in the refractive index of the section. For example, if the apparent depth is an optical path length through the aqueous humor, a change in the refractive index of the aqueous humor may be derived from a comparison of optical path length measurements, thereby providing a measure of the glucose concentration of the aqueous humor. In this case, the first and second surfaces are the cornea-aqueous humor interface and the aqueous humor-ocular lens interface respectively. Although the method and apparatus of the present invention are intended to be used predominantly with the human eye, the invention may also be applied to animal eyes.

The present invention provides many advantages over previous techniques. For example, the present invention is capable of providing very high (sub-micrometre) axial resolution. In addition, it is not necessary to measure the absolute intensity of the reflected light; the signal profile is instead used primarily to determine the apparent positions of interfaces of the eye. As such, the method is relatively less affected by atmospheric conditions and other changes to the outside of the eye. Furthermore, corneal changes, for example, may be deconvolved from the measurement of the apparent depth of the section. Finally, a laser source is not essential for the present invention.

According to a second aspect of the present invention, there is provided an apparatus for measuring changes in an apparent depth of the anterior chamber of an eye, the anterior chamber being defined by a first interface between the cornea and the aqueous humor of the eye and a second interface between the aqueous humor and the ocular lens of the eye, the apparatus comprising: a) an optical focusing assembly, adapted to focus incident light to a measurement location proximate or within the eye; b) a scanning assembly, adapted to scan the measurement location through the anterior chamber; c) a detector, adapted to detect reflected light from the measurement location as the measurement location passes through the first and the second interfaces and adapted to generate a signal representative of the detected light; and d) a processor, adapted to: i) derive from the signal apparent positions of the first and the second interfaces and, therefrom, the apparent depth of the anterior chamber; ii) compare the derived apparent depth with a previous reference measurement of the apparent depth, so as to determine a change in the refractive index of the aqueous humor; and iii) calculate a measure of change in concentration of an analyte of interest in the aqueous humor from the determined change of refractive index.

In preferred embodiments, the apparatus employs a confocal arrangement, so that the location to which and from which light is incident and reflected may be precisely determined. Preferably, the measurement location is scanned by translating an optical lens on a scanning stage.

According to a third aspect of the present invention, there is provided a method of measuring changes in a property of an eye, comprising the steps of: a) directing light from a light source to a first reference location; b) spatially filtering light not received at the first reference location;

c) receiving light from the first reference location and focusing the light to a measurement location; d) scanning the measurement location along a measurement line within the eye; e) receiving reflected light from the measurement location and focusing the reflected light to a second reference location; f) spatially filtering reflected light not received at the second reference location; g) measuring an intensity of the reflected light received at the second reference location; h) relating an intensity measurement to an apparent position of the measurement location; i) selecting intensity measurements of interest, the intensity measurements of interest representing measurement locations of interest; and j) deriving a distance between the measurement locations of interest, the distance being an apparent depth of the anterior chamber, the anterior chamber being defined by a first interface between the cornea and the aqueous humor of the eye and a second interface between the aqueous humor and the ocular lens of the eye, the method further comprising the steps of: k) comparing the derived apparent depth with a previous reference measurement of the apparent depth, so as to determine a change in the refractive index of the aqueous humor; and l)

calculating a measure of change in concentration of an analyte of interest in the aqueous humor from the determined change of refractive index.

Preferably, the method employs a confocal scanning technique and the first and second reference locations are coincident. Preferably, the intensity measurements of interest are peaks in the reflected light intensity profile which is obtained, each peak representing a respective interface between different refractive regions of the eye.

According to a fourth aspect of the present invention, there is provided an apparatus for measuring changes in a property of an eye, the property being an apparent depth of the anterior chamber defined by a first interface between the cornea and the aqueous humor of the eye and a second interface between the aqueous humor and the ocular lens of the eye, the apparatus comprising: a light source; a source optical element, adapted to direct light from the light source to a first reference location; an objective optical element, adapted to receive light from the first reference location and to focus the light to a measurement location, the objective optical element being further adapted to scan the measurement location along a measurement line within the eye and through the anterior chamber; a return optical element, adapted to receive reflected light from the measurement location and to focus the reflected light to a second reference location; an optical detector, adapted to measure an intensity of the reflected light received at the second reference location; and a processor, adapted to: i) relate intensity measurements of interest to apparent positions of the measurement location, so as to derive the apparent depth of the anterior chamber; ii) compare the derived apparent depth with a previous reference measurement of the apparent depth, so as to determine a change in the refractive index of the aqueous humor; and iii) calculate a measure of change in concentration of an analyte of interest in the aqueous humor from the determined change of refractive index.

Preferably, the apparatus employs a confocal scanning arrangement and the first and second reference locations are coincident. Advantageously, the reference locations are provided by a pinhole aperture, which also acts to stop stray light (i.e. light not focused to the reference locations) from continuing past the reference locations.

According to a fifth aspect of the present invention, there is provided a method of measuring an apparent depth of a section of an eye, the section being defined by a first curved interface having a centre of curvature and a second virtual interface located at the centre of curvature of the first interface, the method comprising the steps of: a) focusing light to a measurement location proximate or within the eye; b) scanning the measurement location through the section; c) detecting reflected light from the curved interface when the measurement location is coincident with that curved interface; d) detecting reflected light from the curved interface when the measurement location is coincident with the centre of curvature of the curved interface; e) generating a signal representative of the detected light; and f) deriving from the signal apparent positions of the first and second interfaces such that a distance between the curved interface and its centre of curvature may be derived.

According to a sixth aspect of the present invention, there is provided a method of measuring an apparent depth of the ocular lens of an eye, the lens being defined by a first interface between the aqueous humor and the ocular lens of the eye and a second interface between the ocular lens and the vitreous humor, the method comprising the steps of: a) focusing light to a measurement location within the eye; b) scanning the measurement location through the ocular lens; c) detecting reflected light from the measurement location as the measurement location passes through the first and the second interfaces and generating a signal representative of the detected light; and d) deriving from the signal apparent positions of the first and the second interfaces and, therefrom, the apparent depth of the ocular lens.

The apparatus of the present invention may be used in a variety of applications. Preferably, the apparatus is compact and portable. In particular, the apparatus of the present invention may be formed of components using micro-electromechanical systems (MEMS), or micro-systems technology (MST), and may additionally or alternatively be incorporated in a hand-held device, and these features represent further aspects of the present invention.

Other preferred features are set out in the description, and in the dependent claims which are appended hereto.

BRIEF DESCRIPTION OF THE DRAWINGS

The present invention may be put into practice in a number of ways and some embodiments will now be described, by way of example only, with reference to the following figures, in which.

DETAILED DESCRIPTION OF THE PREFERRED EMBODIMENTS

Figure 1:
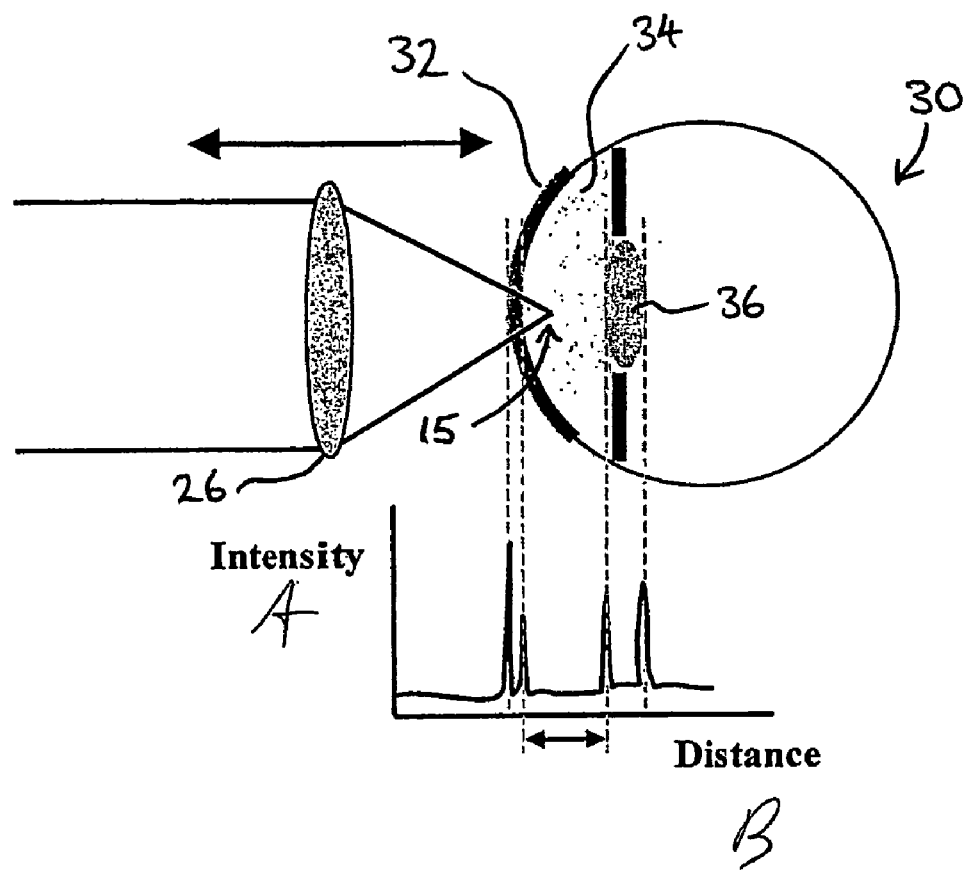
FIG. 1 shows schematically a scanning technique in accordance with a first embodiment of the present invention.

FIG. 1 shows an embodiment of the present invention, in which a scanning technique is used to measure the apparent locations of interfaces within an eye 30. Incident light is focused to a location, which represents a measurement volume, generally proximate or within the eye 30. The measurement location is then scanned through at least a part of the eye 30 such as the anterior chamber of the eye. Each time the focused light encounters an interface of the eye 30, the light is reflected from the interface. The reflected light is then detected to generate a signal representative of that detected light. The apparent location of the measurement volume, as determined externally of the eye 30, is related to the signal, so that a reflected light signal profile, with respect to the apparent position of the measurement location, may be generated and, from this, the apparent locations of the interfaces determined. An optical path length, or depth, between any two interfaces of interest may then be calculated.

FIG. 1 shows a scanning lens 26, the focal point 15 of which represents the measurement location. The scanning lens 26 may be scanned along its optical axis (not shown), so that its focal point 15 is, in turn, scanned from a location external of the eye 30 to a location within the eye. With reference to the anterior chamber of the eye 30, the eye comprises a cornea 32, aqueous humor 34 and an ocular lens 36, behind which is the vitreous humor. In this embodiment, the line of measurement taken by the measurement location passes through the cornea 32, the aqueous humor 34 and the ocular lens 36 and is coaxial with the optical axis of the scanning lens 26. As the focal point 15 passes through a surface bounding two media having different refractive indices $n_1$, $n_2$, the incident light is reflected from the surface. A light intensity detector 20 (not shown) detects the reflected light and generates a signal, which rises to a peak and then falls away each time the measurement location passes through an interface in the eye 30. The size of the intensity spike depends on the properties of the two media either side of the interface. Scanning the measurement location therefore results in a reflection peak for each of the four surfaces illustrated in FIG. 1: the air-cornea boundary, the cornea-aqueous humor boundary, the aqueous humor-ocular lens boundary, and the ocular lens-vitreous humor boundary. The apparent distance between features of interest on the intensity curve may then be determined and properties of the eye 30, such as corneal thickness, ocular lens thickness, or the optical path length, l, through the aqueous humor 34, may be derived.

The optical path length, l, through the aqueous humor is given by the distance between the intensity peaks seen when the reflected light is from the cornea-aqueous humor interface and the aqueous humor-ocular lens interface. The intensity curve shown in FIG. 1 is characteristic of the reflected light intensity measured between the exterior surface of the cornea 32 and the surface between the ocular lens 36 and the vitreous humor (when secondary, retro-reflections from these curved surfaces, which are discussed below, are ignored). As such, the two intensity measurements of interest are the middle two intensity peaks of the four and the distance between these peaks will be referred to as the optical path length l.

The optical path length l is the product of the physical thickness, d, of the aqueous humor 34 and the refractive index, n, of the aqueous humor: $l=nd$. From individual to individual, the physical thickness d varies in dependence upon a number of factors, including the individual's particular physiology, the corneal thickness and the accommodation of the ocular lens. As a general rule, the cornea 32 increases in thickness by approximately 5% overnight and requires around four hours to return to its baseline thickness. A number of proposed techniques for the measurement of glucose levels in the aqueous humor are affected by this phenomenon, to the extent that their accuracy is compromised. One advantage of the scanning technique of the present embodiment is that the corneal thickness may be measured independently and thus deconvolved from the measurement of the optical path length l of the aqueous humor 34.

Other factors which may affect the properties of the cornea 32, the aqueous humor 34 and the ocular lens 36 may also be deconvolved from the optical path length l measurements. For example, the wearing of contact lenses changes the thickness of the cornea 32. Using the scanning technique of the present embodiment, both this effect and the fact that an additional optical component is present along the measurement line may be taken into account and factored out of the optical path length l measurement. Similarly, by arranging for the measurement line to extend partially into the vitreous humor, the locations of both surfaces of the ocular lens 36 may be determined. The thickness of the ocular lens 36 can then be evaluated and taken into account in the optical path length l measurement. Alternatively, a reference object 38 (not shown) may be used to achieve a reference accommodation of the eye 30. By arranging the reference object 38 so that it appears to be located at infinity and so that it is visible by the eye 30 throughout a scanning measurement, it is possible for the eye to maintain a constant, reference accommodation (i.e., the ocular lens 36 should repeatably adjust to substantially the same thickness when focusing the reference object 38). This also provides the advantage that the eye 30 is looking in a predetermined direction and not to one side (i.e., the eye is properly aligned), which helps to ensure that reflected light is properly received by the detector 20.

Preferably, in this embodiment, a light source (not shown) provides an incident beam of light, which is passed through a first reference location 11 (not shown) defined in space. The incident light beam is then manipulated by at least the scanning lens 26 to generate a converging light beam, which is irradiated to the eye 30. Preferably, a spatial filter (not shown) is used to prevent incident light not passing through the first reference location 11 from being focussed to the eye 30. The point 15 to which the light beam is focused is scanned along a measurement line through the eye 30, from a position in front of the cornea 32 to behind the ocular lens 36. During this operation, the apparent distance moved by the focus 15 and the intensity values of the backward scattered light beam received at the detector 20 are logged. Preferably, the reflected light is arranged to pass through a second reference location 13 (not shown), which may be traced directly back to the first reference location 11. Again, it is preferable that a spatial filter (not shown) is used to prevent reflected light not passing through the second reference location 13 from being received at the detector 20. In this way, it may be established that light which is received at the detector 20 has passed through the second reference location 13 and has, therefore, also passed through the first reference location 11. Since light passing through the first reference location 11 is focused to the measurement location, any light received at the detector 20 should have been reflected from the measurement location and should, therefore, indicate the presence of an interface. Of course, there will be a relatively low, background level of light detected by the detector 20, but the surface reflections will result in a much greater intensity signal, so there is no degradation in measurement accuracy as a result of this. The distance moved between the intensity peaks seen when the back surface of the cornea 32 and the front surface of the ocular lens 36 respectively are in focus gives the optical path length l through the aqueous humor 34.

If the physical thickness d of the aqueous humor 34 is constant, or if changes to its thickness caused by variations in the cornea 32 and/or the ocular lens 36 are measured and taken into account, any changes in the optical path length l measurement are due to changes in the refractive index n of the aqueous humor. Therefore, once a calibration measurement of the optical path length l, refractive index n, and physical thickness d of the aqueous humor has been taken, changes in the refractive index may be determined. Since there is a linear relationship between the concentration of glucose within the aqueous humor 34 and its refractive index n, changes in the glucose concentration may be derived from the changes in refractive index. Then, because the glucose concentration in the aqueous humor 34 is, in turn, dependent on the glucose concentration in the bloodstream of a patient, changes in the blood glucose concentration may be determined. In this way, the patient may check his blood glucose level and discover whether any corrective action is required, should the level be outside acceptable limits.

There are a number of ways of performing the patient calibration. One preferred method involves taking several measurements of the optical path length l and, for each measurement, also taking a blood sample, from which the blood glucose concentration may be derived. The range of measurements should cover the expected range of blood glucose concentrations of a diabetic patient. The optical path length l may be measured directly, but the physical thickness d and the refractive index n may not be resolved independently from a single optical path length measurement. It is therefore assumed that the physical thickness d does not change by an appreciable amount between measurements, so that there is a direct correlation between the range of measurements of the optical path length l and the derived blood glucose levels. The correlation curve, which is generally a straight line, may then be used for future optical path length measurements—taken without a corresponding blood sample—to determine the blood glucose concentration of the patient.

Figure 2:
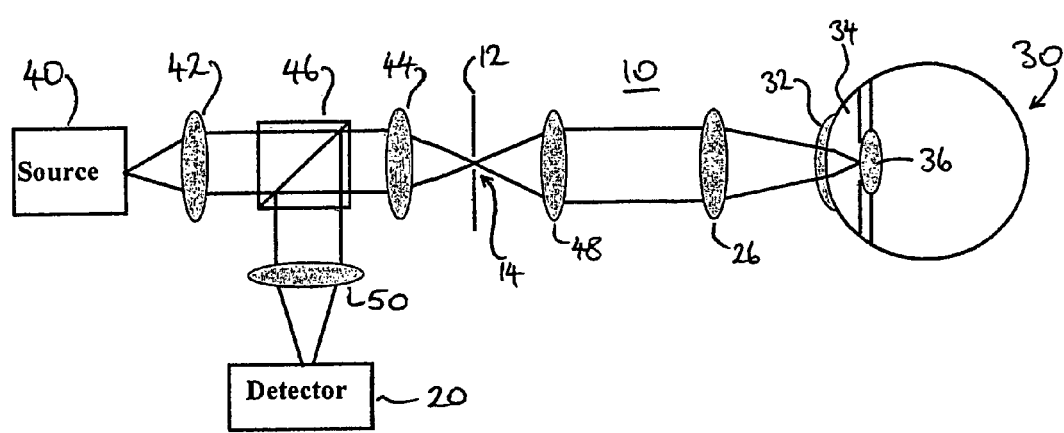
FIG. 2 shows a confocal optical scanning apparatus in accordance with a second embodiment of the present invention.

As will be understood, there are many different embodiments which may be used to put the apparatus and method of the present invention into practice. FIG. 2 shows one exemplary embodiment, which in detail comprises a confocal scanning apparatus. Throughout this specification, identical or similar items are referred to using the same reference numeral. The apparatus comprises a light-emitting diode (LED) light source 40, which is arranged to emit light in the red region of the visible wavelength spectrum. Diodes which may be used include the Hamamatsu L7140 10 650 nm optical link LED (manufactured by Hamamatsu Photonics K.K. of Japan) or the Opto Diode Corporation OD 520 L high output green LED (manufactured by Opto Diode Corp. of California, USA), although, for certain applications, proprietary light sources may be designed and used. This wavelength region is chosen in order to minimise the possibility of causing chronic damage to the eye 30. In addition, red light is preferred, since there is a relatively large choice of LEDs in this wavelength region. However, light at other visible wavelengths, down to and including green light, may alternatively or additionally be used, especially for embodiments using two wavelengths of light (such as FIG. 3, below), since this offers a desirable separation between the two wavelengths.

A source collimating lens element 42 is located downstream of the light source 40 and is used to collimate the light into an incident light beam having a defined beam size. A source convergent lens element 44 is then used to bring the light beam to a first reference location 11, at the focal point of the convergent lens element. Disposed in between the two lens elements 42, 44 is a beam splitter 46. The beam splitter 46 may be provided by a BK7 broadband AR coated 50/50 beam splitter, such as a 25 mm side Linos cube, number 35 5525 (manufactured by LINOS Photonics GmbH & Co. KG of Germany). However, in certain applications, a custom-made beam splitter may be used.

The term "beam splitter" is generally used to refer to an optical element which divides an incident light beam. The ratio of reflected light to transmitted light in any chosen direction may be adjusted according to the particular functional requirements of the beam splitter. In the present embodiment, the beam splitter 46 is arranged to permit 50% of the incident light beam to pass through the beam splitter, from the source collimating lens element 42 to the source convergent lens element 44, substantially undeviated. For light returning through the source convergent lens element 44 (this acting as a return collimating lens element), the beam splitter 46 is arranged to redirect 50% of the return light by 90 E towards a detector convergent lens element 50, which focuses the return light to the detector 20. In an alternative embodiment, a polarising beam splitter, followed by a quarter-wave plate is used, in order to reduce the amount of light lost during combination and redirection.

Located at a first reference location 11 is the pinhole aperture 14, provided by the pinhole stop 12, which lies in the focal plane of the source convergent lens element 44. The diameter of the pinhole aperture 14 is determined by the required numerical aperture (NA) of the incident light beam and the wavelength of light used. In this embodiment the diameter is of the order of 10 µm.

From the first reference location 11, incident light is collimated by an objective collimating lens element 48 and focused to a measurement location by the objective convergent lens element 26. The measurement location lies on a measurement line, which is coaxial with the optical axis of the lens arrangement 10. Preferably, the optical axis of the eye 30 is also coaxial with the optical axis of the lens arrangement 10, such that the measurement line passes from outside the eye, through the centre of the cornea 32, through the aqueous humor 34 and through the centre of the ocular lens 36. If desired, the measurement line may continue through the ocular lens 36 and partially into the vitreous humor, so that measurements of the thickness of the ocular lens may be taken.

When a surface of, or in, the eye 30 is present at the measurement location, provided by the second focal point 15 of the lens arrangement 10, incident light is reflected and focused to a second reference location 13. In this embodiment, the second reference location 13 is provided by the pinhole aperture 14 and is thus confocal with the first reference location 11. The return light beam is reflected from the surface of, or in, the eye 30 and passed along its original path, through the pinhole aperture 14 and to the beam splitter 46, where the return light is redirected by 90 E and focused by the detector convergent lens element 50 to the detector 20. The detector 20 measures the intensity of the return light, which is linked to the apparent measurement location by any suitable means, such as a processor.

The objective convergent lens element 26 is mounted on a scanning stage 24 (not shown), so that the lens element may be translated backwards and forwards. In this way, the measurement location may be scanned along the measurement line, through the eye 30. In a preferred configuration of the lens element 26, the incident light beam exiting the lens element has an initial diameter of 7 mm and NA=0.2.

In order to obtain a reflected light intensity profile of the eye 30, the objective convergent lens element 26 is scanned by the scanning stage 24, so that the measurement location is translated from a point external of the eye, in front of the cornea 32, to a point within the ocular lens 36. While the scanning stage 24 translates the lens element 26, the position of the scanning stage is measured by a sensor 52 (not shown). This positional information is sent to a processor 54 (not shown), which also receives intensity signals from the detector 20, so that the location of the objective convergent lens element 26 and hence its focal point 15 (which represents the measurement location of the optical arrangement 10) in relation to component features of the eye 30 is known throughout the measurement process.

Each time a component feature of the eye 30, such as the air-cornea interface or the aqueous humor-ocular lens interface, is coincident with the measurement location, an intensity peak is seen. For measuring the distance between features of interest of the eye 30, it is not necessary to measure the absolute intensity of the reflected light reaching the detector 20; the information required is provided by the lateral position of the centre of each peak representing a feature of interest. During scanning, the measurement location is associated with the intensity being measured at the detector 20 and the apparent location of the surfaces of components of the eye 30 are thereby determined.

In order to improve the accuracy of the intensity measurements taken, curve fitting may optionally be used to increase the resolution with which the peak of each intensity spike is determined.

The distance between the intensity peaks generated by reflections from the back surface of the cornea 32 (the cornea-aqueous humor interface) and the front surface of the ocular lens 36 (the aqueous humor-ocular lens interface) represents the optical path length l through the aqueous humor 34. If the accommodation of the eye 30 is maintained throughout a measurement and is consistent for all measurements, then the physical depth of the aqueous humor is a constant and the only variable is the refractive index n of the aqueous humor. As such, changes in the refractive index n—measured as changes in the optical path length l—may be linked to changes in the glucose level. In order to achieve this, it is necessary first to perform an individual calibration for each patient, to ascertain the particular relationship between the optical path length l and the blood glucose concentration.

Figure 3:
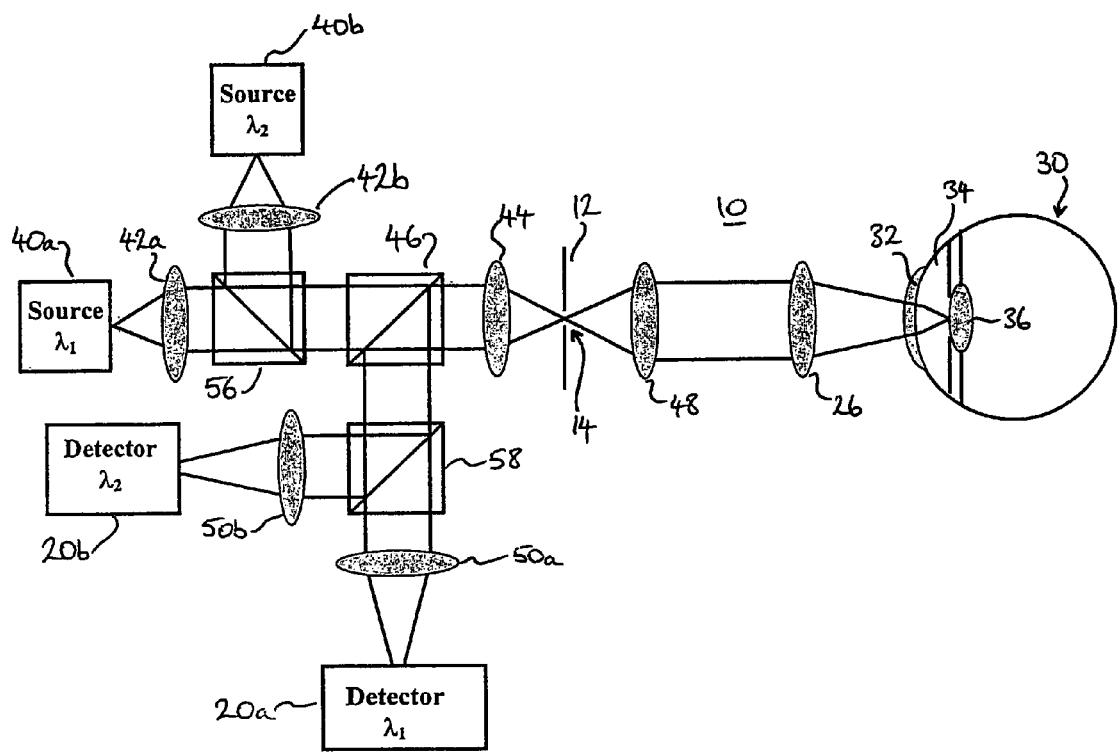
FIG. 3 shows a confocal optical scanning apparatus in accordance with a third embodiment of the present invention.

In order to provide increased resolution to the measurements and to make the ocular property-measuring instrument more useful, two wavelengths, $\lambda_1$ and $\lambda_2$, may be used to perform two optical path length measurements simultaneously. One such embodiment is shown in FIG. 3. The instrument is similar to that shown in FIG. 2, but differs in the following details:

The light source 40 and source collimating lens element 42 have been replaced by a first light source 40a and first source collimating lens element 42a, a second light source 40b and second source collimating lens element 42b, and a beam combiner 56. These components are disposed upstream of the beam splitter 46, as before. The first and second light sources 40a, b and collimating lens elements 42a, b respectively are arranged such that their optical axes are mutually perpendicular. In this way, a first light beam having a first wavelength, $\lambda_1$, is received at the beam combiner 56 along an optical axis which is generally coaxial with that of the lens arrangement 10. A second light beam, having a second different wavelength, $\lambda_2$, is received at the beam combiner 56 along an optical axis generally perpendicular to that of the lens arrangement 10. The two light beams are combined and the combined light beam passes through the beam splitter 46 and onwards in the manner described above. On reflection from a surface of the eye 30 and receipt by the beam splitter 46, the combined return light beam is redirected by substantially 90 E, again as before. However, in this embodiment, the detector convergent lens element 50 and detector 20 have been replaced by a first detector convergent lens element 50a and detector 20a, a second detector convergent lens element 50b and detector 20b, and a detector beam splitter 58. Return light from the beam splitter 46 is received by the detector beam splitter 58, which separates the return light into two (still combined) perpendicular light beams, for focusing and detection. The first and second detectors 20a, b may comprise any suitable filter means (not shown) for permitting light of one wavelength only ($\lambda_1$ and $\lambda_2$ respectively) to be detected. Alternatively, the detector beam splitter 58 may separate the return light beam by wavelength and produce two light beams having the first and second wavelengths $\lambda_1$, $\lambda_2$ respectively.

As for the single wavelength measurement, the intensity profiles measured are matched to the measurement location and the apparent location of the surfaces of interest in the eye 30 are determined for each wavelength. These independent measurements of the optical path length $l_1$, $l_2$ of the aqueous humor 34 are thus made and from these measurements, two simultaneous equations may be obtained and solved. Since the refractive index n of the aqueous humor 34 varies with the wavelength of the incident light, the two simultaneous equations both include three variables: the refractive index $n_1$, $n_2$ at each wavelength $\lambda_1$, $\lambda_2$ and the thickness d of the aqueous humor 34. However, as the refractive indices $n_1$, $n_2$ are dependent on wavelength and are therefore related to each another, the two simultaneous equations may be solved and the refractive index and thickness of the aqueous humor determined.

One approach for analysing the two equations obtained when two wavelengths, $\lambda_1$, $\lambda_2$, are used is as follows. The two equations obtained are:

$$l_1 = d n_{\lambda 1}$$

$$l_2 = d n_{\lambda 2}$$

where d is the (constant) physical thickness of the aqueous humor 34 and $l_1$ is the optical path length and $n_{\lambda 1}$ is the refractive index for wavelength $\lambda_1$, and $l_2$ is the optical path length and $n_{\lambda 2}$ is the refractive index for wavelength $\lambda_2$. Since the physical thickness d is the same in both cases and $l_1$ and $l_2$ are both measured, the two variables which are to be solved are $n_{\lambda 1}$ and $n_{\lambda 2}$. The two refractive indices $n_{\lambda 1}$, $n_{\lambda 2}$ are related to each other by the dispersion curve for the particular concentration of glucose solution in the aqueous humor 34, the relationship taking the form:

$$V = f(n_{\lambda 1}/n_{\lambda 2}).$$

Therefore, by using a look-up table, or equation for the dispersion relation for different glucose concentrations, the ratio of the refractive indices $n_{\lambda 1}$, $n_{\lambda 2}$ at the two wavelengths $\lambda_1$, $\lambda_2$ can be used to calculate the glucose concentration of the aqueous humor 34.

Removing the physical distance d from this calculation provides an important benefit, since this value cannot accurately be assumed to be constant in all circumstances. In practice, the cornea 32 changes thickness diurnally, the ocular lens 36 oscillates regularly by a small amount and, during testing, a user may unintentionally move the test instrument or his head. Because both wavelength measurements are taken simultaneously, any variation in the value of the physical thickness d of the aqueous humor 34 will affect both measurements of the optical path length l equally and will therefore be cancelled out upon division of the two measurements.

As will be understood, the optical path length measurements need to be calibrated for each patient before use. This is achieved by simultaneously taking finger stick blood tests and performing the eye scan, while the blood glucose level is varied. In this way, the blood glucose level may be directly related to the measured optical path length, or refractive index ratio without the need to determine the intermediate values of the glucose concentration of the aqueous humor itself.

In addition, by using more than two wavelengths of incident light, it is possible to determine still other properties of the eye 30, such as the levels of ascorbate, pyruvate, lactate, and other chemicals, including medically or intentionally introduced drugs as well as naturally occurring ones. It is also possible to determine refractive index changes taking place as a result of changes in ambient temperature and pressure. In this way, N simultaneous equations may be generated, with N independent variables, and these may be solved to determine changes in properties of the eye 30. If m different properties of the aqueous humor 34, for example, are to be evaluated, m+1 measurement wavelengths should be used.

Principles behind the confocal scanning technique embodied by the apparatus of FIG. 2 and the apparatus of FIG. 3 will now be described in some detail with reference to FIGS. 4a, 4b and 5.

Figure 4A:
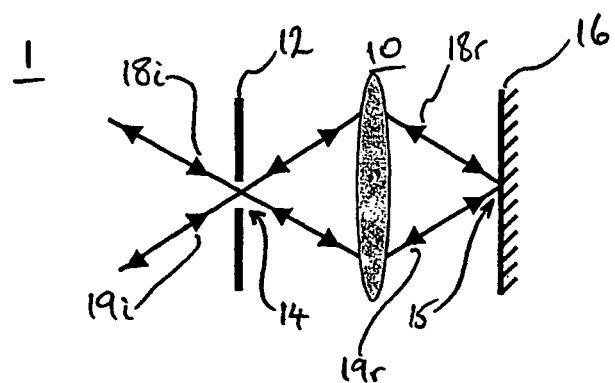
FIGS. 4a and 4b show schematic ray diagrams of a confocal lens arrangement, with a reflecting object respectively in and out of focus.

FIG. 4a shows an optical configuration 1, which includes a lens arrangement 10, schematically illustrated by a single lens, and a pinhole stop 12 having a pinhole aperture 14 disposed therein. The pinhole stop 12 is positioned in relation to the lens arrangement 10, such that the pinhole stop lies in the first focal plane of the lens arrangement and the pinhole aperture 14 lies on the optical axis (not shown) of the lens arrangement. In this way, light passing through the pinhole aperture 14 is received by the lens arrangement 10 and focused to its second focus 15. Located at the second focal plane of the lens arrangement 10 is a reflecting object 16, from which incident light is reflected.

The optical configuration 1 shown in FIG. 4a is a confocal arrangement, with the reflecting object 16 in focus. The lens arrangement 10 functions both as the objective imaging element, for light incident upon the reflecting object 16, and as the return imaging element, for light reflected from the reflecting object. The pinhole aperture 14 defines a first reference point in space, past which incident light upstream of the optical configuration 1 must travel to reach the reflecting object 16, and past which reflected light from the reflecting object must travel in order to be detected.

FIG. 4a shows two incident light rays 18i, 19i and two reflected light rays 18r, 19r propagating through the optical configuration 1 in the above manner. The incident light rays 18i, 19i are made to converge at the first reference point provided by the pinhole aperture 14 by an upstream focusing element (not shown). From here, the incident rays 18i, 19i pass through the lens arrangement 10, which refracts and focuses the rays to the second focus 15. Because the second focal point 15 of the lens arrangement 10 is located at a point on the reflecting object 16, the incident light rays 18i, 19i are reflected from the reflecting object. The reflected light rays 18r, 19r are received by the lens arrangement 10 and focused to a second reference point. In the confocal arrangement shown in FIG. 4a, the second reference point is also provided by the pinhole aperture 14 and is therefore coincident with the first reference point.

In this example, the path described by incident light ray 19i represents a reflection about the optical axis of the lens arrangement 10 of the path described by incident light ray 18i. As such, on reflection from the reflecting object 16, reflected light ray 18r follows the path described by incident light ray 19i and reflected light ray 19r follows the path described by incident light ray 18i. In this way, incident light rays 18i, 19i and reflected light rays 18r, 19r describe complementary paths through the optical configuration 1. Thus, if a reflecting object 16 is present at the second focus 15 of the lens arrangement 10, an incident light beam propagating through the pinhole aperture 14 and lens arrangement will be reflected back along its original path and return through the pinhole aperture.

The reflecting object 16 need not be a polished surface or mirror, but may be any surface from which light is reflected. In particular, the reflecting object 16 may be a surface of a transparent medium having a different refractive index from its surroundings, such that a Fresnel reflection occurs when light is incident upon the surface.

If no reflecting object 16 is present at, or near, the second focus 15 of the lens arrangement 10, light is not reflected from that point back through the lens arrangement towards the pinhole stop 12 and only a negligible amount of light passes through the pinhole aperture 14 itself. If the reflecting object 16 is proximate, but not coincident with, the second focal point 15, the path described by a light beam through the optical configuration 1 is as shown in FIG. 4b. Here, incident light rays 18i, 19i pass through the pinhole aperture 14 and are focused by the lens arrangement 10 in the same manner described with reference to FIG. 4a. However, since there is no reflecting object 16 present exactly at the second focus 15, the incident light rays 18i, 19i continue in a downstream direction, past the second focus, until they shortly encounter the reflecting object. Here, the incident light rays 18i, 19i are respectively reflected and return as reflected light rays 18r, 19r. However, since the incident light rays 18i, 19i are not reflected at the second focus 15, the reflected light rays 18r, 19r do not follow the paths described by the incident light rays, as before. As such, the reflected light rays 18r, 19r are not brought to the second reference point provided by the pinhole aperture 14, but are instead brought to separate points on the pinhole stop 12, either side of the pinhole aperture, where conventional absorption or diffuse reflection takes place. Thus, if a reflecting object 16 is close to, but not coincident with, the second focus 15 of the lens arrangement 10, an incident light beam propagating through the pinhole aperture 14 and the lens arrangement will not be reflected back along its original path and through the pinhole aperture. Instead, the reflected light beam will not be focused on the pinhole aperture 14 and only a relatively small proportion of the light will pass through the pinhole aperture.

If a light intensity detector 20 (not shown) is placed upstream of the optical configuration 1, along with suitable optical imaging elements (also not shown), an intensity of the reflected light received through the pinhole aperture 14 may be measured. Depending on the presence of, and exact location of, a reflecting object 16, the intensity measured will be either a negligibly small, minimum value (for no object), a peak value (for an object coincident with the second focus 15), or a value between the minimum and peak values (for an object close to the second focus). Thus, if the second focus 15 of the lens arrangement 10 is scanned linearly past a reflecting object 16, an intensity curve may be generated.

Figure 4B:
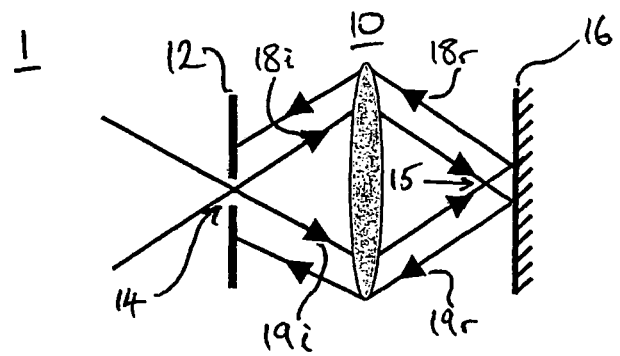
Figure 5:
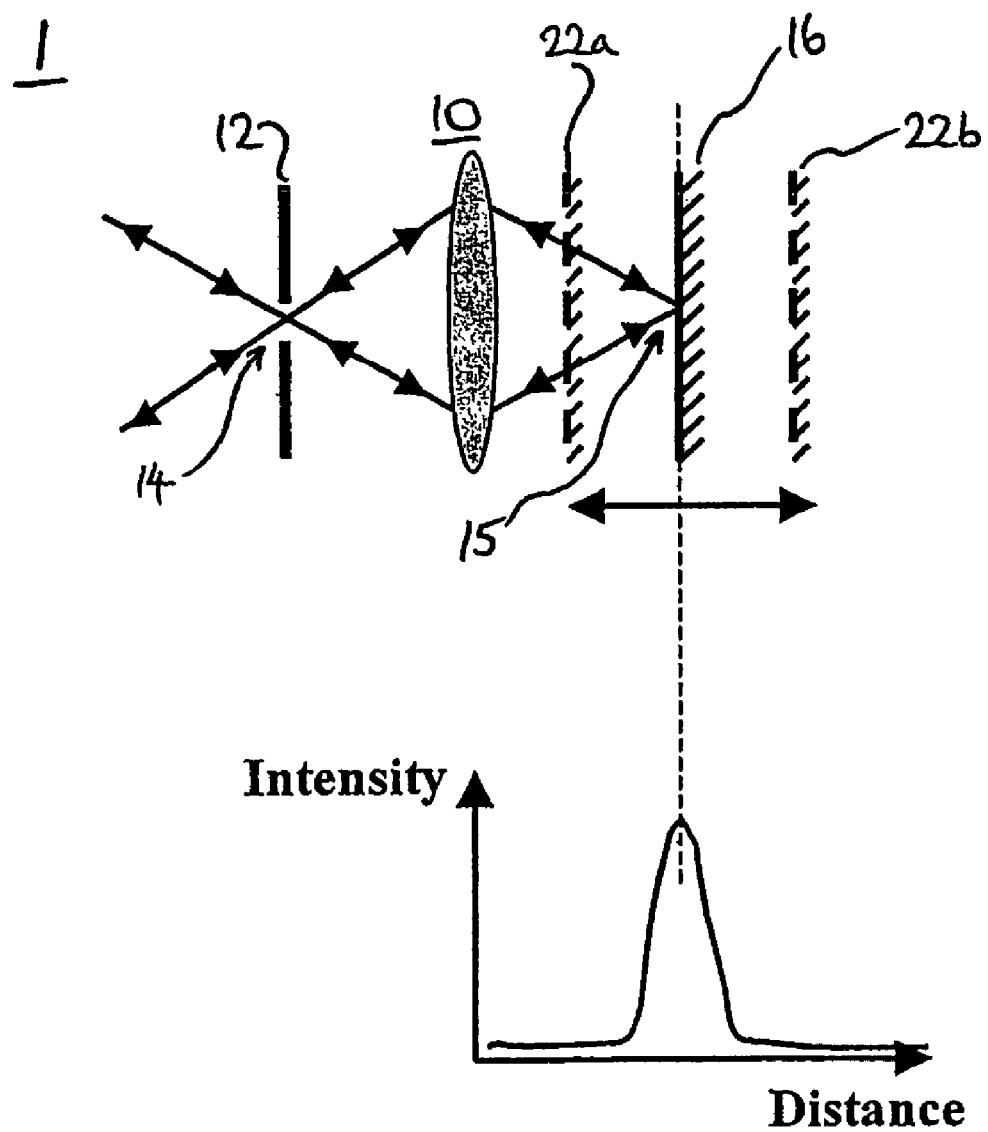
FIG. 5 shows schematically an intensity profile of reflected light when the focal plane of the lens arrangement of FIGS. 4a & 4b is scanned past a reflecting object.

FIG. 5 shows the optical configuration 1 of FIGS. 4a and 4b, arranged to scan the second focal point 15 between first and second focal planes 22a and 22b. In this embodiment the lens arrangement 10 includes a mechanical translation means 24 (not shown), which is arranged to translate at least a final, convergent lens element 26 (also not shown) along a predetermined path, in either of a forward or a rearward direction. The geometry of the lens element 26 is fixed, such that a radius of curvature of the wavefronts of the incident light leaving the lens element is predefined. In this way, the focal length of the lens arrangement 10 is a known constant. Therefore, by knowing the location of the lens element 26 during translation, the exact position of the second focus 15 may also be known.

When the light intensity detector 20 is positioned upstream of the optical configuration 1, and the second focal point 15 is scanned linearly from the first focal plane 22a to the second focal plane 22b, the intensity measurements made by the detector are paired with the varying position of the second focus 15. This may be achieved by moving either the lens arrangement 10 or the item under evaluation. An intensity curve, as shown in FIG. 5, is thereby generated. The intensity curve illustrates the fact that there is a relatively negligible, background intensity value measured when there is no object present at or near the second focus 15. As the second focus 15 is moved towards the reflecting object 16, the intensity value rises, in line with the object coming increasingly into focus. When the reflecting object 16 and second focal point 15 are coincident, the intensity value reaches a peak value, since the greatest amount of incident light passing through the pinhole aperture 14 and being reflected from the reflecting object is received back through the pinhole aperture. Further scanning of the lens element 24 towards the second focal plane 22b takes the reflecting object 16 increasingly out of focus, so that the intensity curve falls quickly back to the minimum intensity value.

Thus by knowing the design of the lens arrangement 10 and the relative position of the second focus 15, the apparent location of the reflecting object 16 may be established by determining the distance measurement which corresponds with the peak intensity measurement on the curve. The use of the confocal principle in this configuration permits a reference location in space to be defined very precisely. Indeed, it is possible to achieve sub-micrometre axial resolution using such a confocal arrangement.

Figure 6A:
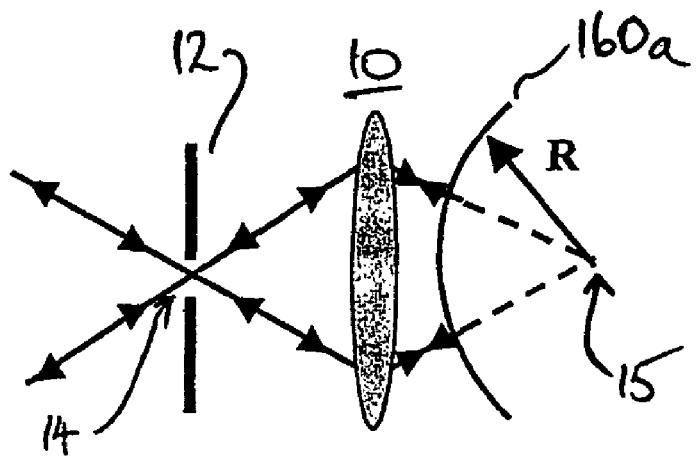
FIGS. 6a and 6b show schematic ray diagrams of retroreflections from a convex surface and a concave surface respectively, when the lens arrangement of Figures and 5 is focused at the centre of curvature of the surface.
Figure 6B:
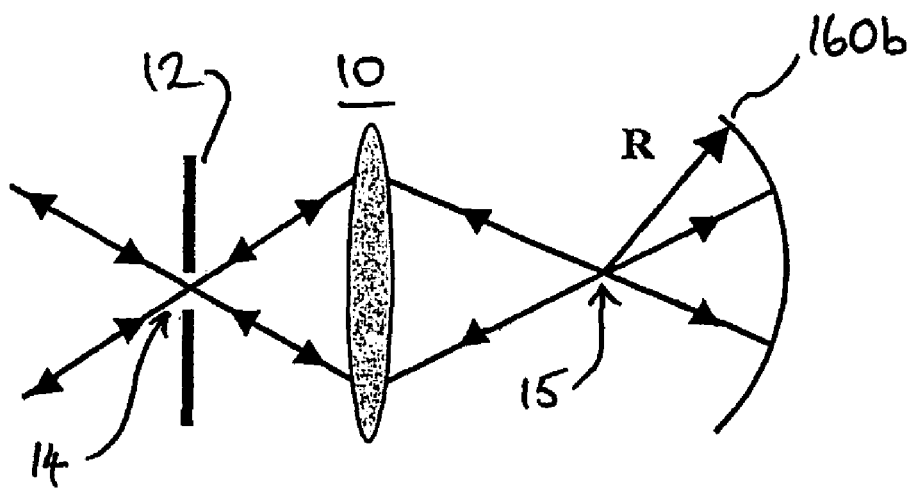

FIGS. 6a and 6b illustrate a further embodiment of the present invention, in which the radius of curvature of a surface (of the eye 30) may be measured. During scanning of the measurement location, provided by the focal point 15, the focal point may be moved into a position which is coincident with the centre of curvature of a curved optical interface of the eye 30, such as a surface of the cornea 32 or the ocular lens 36, for example. In such a position, the incident light rays which converge to the focal point 15 follow a path which is normal to the curved surface 160. As such a proportion of the incident light is retro-reflected from the surface 160 back along its original optical path. FIG. 6a shows an embodiment, in which the curved surface 160 is a convex surface 160a, having a radius of curvature, R. FIG. 6b shows an embodiment, in which the curved surface 160 is a concave surface 160b, also having a radius of curvature, R. In each case, individual light rays are retro-reflected from the surface 160a, b and return along their individual, original paths back through the pinhole aperture 14. As far as the detector 20 and associated processor are concerned, there is a virtual interface located at the centre of curvature in both cases. Thus light appears to be reflected from the measurement location at the virtual interface (at the centre of curvature) and the intensity signal generated by the detector 20 as a result of the retro-reflections is logged as originating from that location.

Thus a reflection peak is again detected by the detector 20, as the light is directed back and passes through the pinhole aperture 14. By tracking the measurement location, the apparent location of the centre of curvature of the surface 160 may be determined from the corresponding light intensity peak. By calculating the distance between this location and the location of the intensity peak observed when the measurement location passes through the curved surface 160, the apparent radius of curvature R' of the curved surface may be determined.

By collecting this information as the measurement location is scanned through the eye 30 as described above, the apparent location of each surface and its radius of curvature may be determined. Since the refractive indices of each component of the eye 30 are already known, this information may be used to determine the refractive errors of a particular eye and, in turn, the power of corrective spectacles which may be required.

Furthermore, this method may be used to detect debris in the aqueous humor 34, caused for example by corrective eye surgery, cataract removal and the like. Currently, such debris is not specifically quantified and ophthalmologists have different views as to what is to be considered a large or small amount of material. With the above scanning technique, the debris is detected as small intensity reflections within the aqueous humor 34 and the number and size of these reflections may be used to quantify the amount of such debris in the aqueous humor.

In order to obtain a strong return signal at the detector 20, it is important that the eye 30 is oriented to be axially aligned with the scanning lens 26. In one embodiment, this is achieved by simultaneously projecting an image to the user whilst taking the measurement, so that the user focuses on this image and the correct alignment and accommodation of the eye is maintained. In an alternative embodiment, two points of light, coaxial with the measurement beam, are projected into the eye 30, so that the user may align the two points before performing the measurement, thereby ensuring correct alignment. In yet another embodiment, a point source of light, coaxial with the measurement beam, is shone through the pinhole and is arranged to be visible only when the user lines up the light with the pinhole aperture 14 (i.e. when the user can see the point source of light). Once this is so, the instrument is correctly aligned.

Axial misalignment results in the return light beam being slightly offset with respect to the pinhole aperture 14 and thus reduces the level return light received by the detector 20. If, however, a CCD array is used instead of the pinhole aperture 14, each pixel within the CCD array can be treated as a pinhole aperture. Accordingly, if the focused return light moves to one side, the pixel considered to be the pinhole aperture may be replaced by a different pixel, thereby tracking the focused return light by tracking the intensity peak. There will be a generally larger background level of light in this case, but the intensity peak may still be detected and tracked by analysing the detected intensities measured by the neighbouring pixels in the array.

Figure 7:
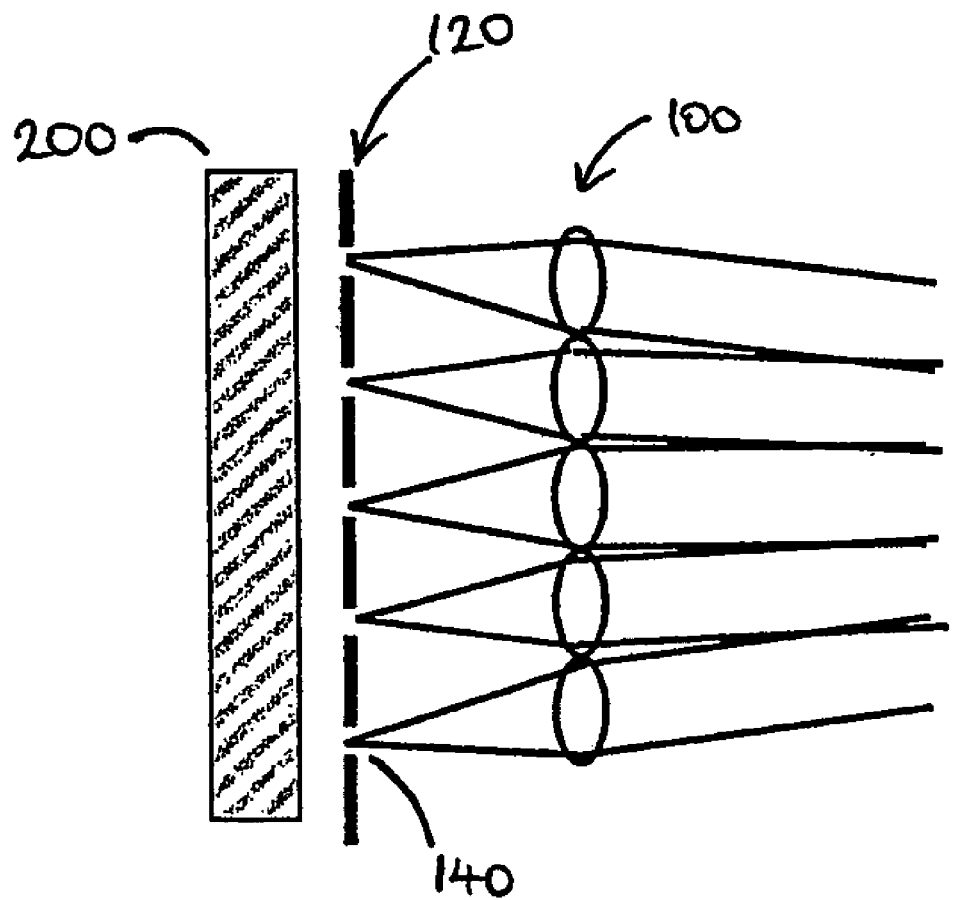
FIG. 7 shows a confocal detector array in accordance with a further embodiment of the present invention.

Alternatively, a further solution to the axial misalignment problem which does not require the user to look straight into the instrument involves the use of an array of micro-lenses 100, in combination with an array of pinhole apertures 120 in the return path and a CCD detector array 200, as shown in FIG. 7. With this arrangement, an array of confocal detectors is provided, with each individual confocal system being arranged to analyse a specific angle of the return light.

It will be understood that the above embodiments can be adapted and enhanced in a number of ways. From a patient's point of view, it may be disconcerting to have a laser shone into an eye, so it is preferable for the apparatus to use an incoherent light source 40. This is acceptable from a functionality perspective, but alternative embodiments may use laser sources. These can be any form of laser, including but not limited to diode lasers, vertical cavity surface emitting lasers (VCSELs) and gas lasers. The narrow waveband of a laser source has the advantage that any chromatic aberrations occurring in the optical system with an incoherent source 40 may be reduced.

In embodiments using an incoherent light source 40 the source may be either a narrow or broad wavelength band type. The possible sources include but are not limited to light emitting diodes (LEDs), incandescent or fluorescent lights, or any broadband, "white light" source. With a broadband source, a wavelength filter, such as an etalon, diffraction grating, thin film filter, de-multiplexer (as used in optical telecommunications), or other design could be used to define a narrow measurement waveband. This filter may be located at or near the source 40 or the detector 20 of the instrument.

There is no specific restriction to the wavelength of light which may be used to perform the measurements, although wavelengths in the red region of the spectrum are preferable, since these minimise the possibility of any long term effects on the eye. The wavelength may alternatively be in the ultraviolet, visible, near infra-red or far infra-red region of the spectrum.

The optical elements used in the instrument are preferably refractive lenses, but in some instances it may be advantageous to use diffractive elements instead. Diffractive elements generally have a shallower profile than the refractive elements and may be easily mass produced by moulding techniques, which offers advantages when large scale production is intended. Alternatively still, graded index lenses may be used, and these have the advantage that they are of high quality, relatively small and economical to use in high quantities.

Although in the above embodiments the first and second reference locations 11, 13 have been described as being provided by the pinhole aperture 14, these may alternatively be provided by one or more fibre optic or other light guide elements. The use of an optical fibre affords the possibility of providing the apparatus in the form of a test instrument body and remote test head. In such an embodiment, the optical components upstream of the first reference location 11 are comprised in the body and the lens arrangement 10, which performs the scanning sequence, is comprised in the test head. As such, the test instrument body could, for example, be located on the earpiece of a pair of spectacles, with the test head being built into the front of the spectacles. The use of a light guide structure permits greater flexibility in terms of the location and direction of the light beams than with free-space optics.

Alternatively still, the function of the pinhole aperture 14 may be achieved using a small aperture source and detector combination. Such an arrangement would result in a simplified apparatus, since there would be fewer components required. However, the degree of freedom available in terms of the optical layout would be reduced.

The scanning of the measurement location may be achieved by many techniques including but not limited to physically moving a lens element or changing the focal length of a lens element. If the lens element 26 is translated, it may be controlled in such a way that the focal point moves while the numerical aperture of the measurement beam remains constant, or the focal point may be moved while the numerical aperture of the beam is also changed.

Alternatively, a variable refractive index element, such as a liquid crystal device, may be used, so that there are no moving parts and the lifetime of the instrument may be advantageously increased.

Alternatively still, in applications using mechanical translation, the distance that the translation stage is required to travel may be reduced by 'folding' the light beam. This may be achieved by employing a mirror assembly, between the convergent lens element 26 and the eye 30, to reflect the light beam twice as it is focussed to the measurement location. At least one of the mirrors in the mirror assembly is arranged to be translated, so that the measurement location is scanned in the above manner. In this way, the travel of the focal point 15 (or, measurement location) may be arranged to be twice that of the mirror travel. This effect can be increased further by 'folding' the light beam more than twice, using a suitable mirror assembly. As will be appreciated, the shorter the translation distance required, the smaller the overall size of the instrument may be, which has particular benefits when used as a hand-held device.

Preferably, with any form of mechanical translation, the lens element 26 is mounted on a linear motion stage to enable the scanning of the focal point 15 through the eye 30. The translation stage may be moved with a range of motion control devices including, but not limited to, piezoelectric crystals, lead screw actuators, DC-micrometer or stepper actuators or voice coils. Examples of suitable, commercially available motion control stages include the Newport CMA-12CC compact motorized actuator (manufactured by Newport Corporation of California, USA) and the Physik Instrumente (PI) M-111.15DG high-resolution micro-translation stage (manufactured by Physik Instrumente (PI) GmbH & Co. KG of Germany). Whilst the stage is translated and the focal point 15 is scanned through the eye 30, the reflected light received by the detector 20 is measured. In one embodiment, the coupling of the signal generated by the detector 20 and the position of the measurement location is achieved by simultaneously measuring the location of the stage and the signal generated by the detector 20. In this way, a point-by-point association between the detector signal and the position of the measurement location is obtained. In an alternative embodiment, the stage is translated at a constant speed and its location at any time is known once the external surface of the cornea 32 has been passed by the measurement location (and the detector 20 generated a corresponding signal peak).

The detector 20 employed in the instrument may be one of a number of detectors, such as a CCD, CMOS, or APD, although others are not excluded. The desirable criteria for the detector 20 are that the detector has a large dynamic range, to be able to distinguish the intensity peaks from the background, and that the response time is fast enough to capture the intensity reading from each point in space as the measurement location is scanned through it. The detector 20 may comprise a single element, a linear array, or a two-dimensional array. If a two-dimensional array is used, each pixel may be interrogated independently and axial misalignment of the eye 30 can be accounted for. In such an embodiment, the system may be configured without a physical pinhole stop 12, since each pixel within a CCD detector, for example, can be treated as the equivalent of a pinhole aperture 14.

While it is preferable for the incident light beam to be reflected so that the return light beam passes back along the original path taken by the incident light beam—that is, the return lens arrangement through which the return light beam passes is preferably provided by the objective lens arrangement 10 through which the incident light beam passes, since this reduces the size and complexity of the instrument—the reflected light beam may be arranged to be focused to the second reference location 13 along a different path. This may be achieved, for example, by disposing the objective lens arrangement 10 to one side of the optical axis of the eye 30 and disposing the return lens arrangement equally and oppositely on the other side of the optical axis of the eye.

In any case, the objective lens arrangement and the return lens arrangement preferably each comprise a compound lens.

Depending on the particular requirement of the ocular property-measuring apparatus, the light source 40 may be arranged to generate light having one of a static, jittered, swept or stepped wavelength. This may be achieved in various ways, including the use of a variable wavelength laser, a diffraction grating, a spectrometer, an etalon, or a wavelength division multiplexer.

The measurement technique may be enhanced by using interferometry, in which a reference light path is used in the measurement apparatus and the two beams are interfered coherently, thereby producing an interference pattern which may be measured. The polarisation of the incident light beam may also be controlled, so that more than one polarisation state is used to perform the measurement and two or more simultaneous equations are obtained. In this way, again, more than one parameter of the eye 30 may be measured. Another possible means for obtaining two or more simultaneous equations so that more than one property of the eye 30 may be measured is to provide an array of optical systems in parallel.

This may be achieved with a micro-lens array 100, in conjunction with a pinhole array 120, arranged to provide an array of confocal test systems, as illustrated in FIG. 7. Light received through the array of pinhole apertures 140 is detected by a detector array 200, such as a CCD detector array.

In order to improve the axial resolution of the measurements taken by the instrument, the incident light beam may be modulated and the detector 20 provided with phase sensitive detection means.

Alternatively, other techniques may be used to define a position in space. Optical coherence tomography (OCT) uses a low coherence source and Michelson interferometer arrangement, in which the reference lens is scanned through the required spatial distance to produce an interference effect and a high intensity response, when the optical path length in the reference arm matches that in the working arm and a reflection is obtained from a surface of the eye 30.

The apparatus of the present invention is intended for use in a number of settings, such as in a hospital or a laboratory, by a doctor or an optician, or privately by an individual patient. As such, the apparatus of the present invention may be fitted onto an optical bench or an examination table (as used by an optician for example), or the apparatus may be more mobile, for use by a patient, either while at home or while out. In particular, the apparatus of the present invention may be contained within a hand-held device and may be battery powered. One particularly advantageous embodiment of the present invention involves the use of micro-electromechanical systems (MEMS), or micro-systems technology (MST). The use of micro-optics, micro-motors and micro-stages to achieve a small apparatus size offers particular benefits when the apparatus of the present invention is used as a hand-held device.

The invention claimed is:

1. A method of measuring changes in an apparent depth of the anterior chamber of an eye, the anterior chamber being defined by a first interface between the cornea and the aqueous humor of the eye and a second interface between the aqueous humor and the ocular lens of the eye, the method comprising the steps of:
   a) focusing light to a measurement location proximate or within the eye;
   b) scanning the measurement location through the anterior chamber;
   c) detecting reflected light from the measurement location as the measurement location passes through the first and the second interfaces and generating a signal representative of the detected light;
   and using a processor:
   d) deriving from the signal apparent positions of the first and the second interfaces and, therefrom, the apparent depth of the anterior chamber;
   e) comparing the derived apparent depth with a previous reference measurement of the apparent depth, so as to determine a change in the refractive index of the aqueous humor; and
   f) calculating a measure of change in concentration of an analyte of interest in the aqueous humor from the determined change of refractive index.

2. The method of claim 1, wherein the analyte of interest is glucose.

3. The method of claim 2, further comprising the step of calculating a measure of change in a concentration of glucose within the bloodstream of a patient.

4. The method of claim 1, wherein the analyte of interest is at least one of a naturally occurring or an intentionally introduced substance.

5. The method of claim 1, wherein the detected light is arranged to comprise substantially only light which has been focused to the measurement location and reflected by an interface of the eye.

6. The method of claim 1, wherein the scanning step (b) is achieved by one of translating a lens; translating a lens and varying a numerical aperture (NA) of the lens; translating a mirror of a mirror assembly; varying a refractive index of a variable refractive index element; or varying a focal length of a variable focal length lens.

7. The method of claim 1, wherein the signal peaks for points where the measurement location is coincident with an interface of the eye.

8. The method of claim 1, wherein the light has a single wavelength.

9. The method of claim 1, wherein the light comprises two or more wavelengths.

10. The method of claim 1, further comprising the prior step of providing a reference image, or object, to be focused by the eye during scanning, so as to enable the eye to be repeatably aligned.

11. An apparatus for measuring changes in an apparent depth of the anterior chamber of an eye, the anterior chamber being defined by a first interface between the cornea and the aqueous humor of the eye and a second interface between the aqueous humor and the ocular lens of the eye, the apparatus comprising:
   a) an optical focusing assembly, adapted to focus incident light to a measurement location proximate or within the eye;
   b) a scanning assembly, adapted to scan the measurement location through the anterior chamber;
   c) a detector, adapted to detect reflected light from the measurement location as the measurement location passes through the first and the second interfaces and adapted to generate a signal representative of the detected light; and
   d) a processor, adapted to:
      i) derive from the signal apparent positions of the first and the second interfaces and, therefrom, the apparent depth of the anterior chamber;
      ii) compare the derived apparent depth with a previous reference measurement of the apparent depth, so as to determine a change in the refractive index of the aqueous humor; and
      iii) calculate a measure of change in concentration of an analyte of interest in the aqueous humor from the determined change of refractive index.

12. The apparatus of claim 11, the scanning assembly comprising a scanning stage, adapted to translate an element of the optical focussing assembly such that the measurement location is correspondingly scanned, wherein the processor is further adapted to track the translation of the element and thereby derive a position of the measurement location.

13. The apparatus of claim 11, wherein the detector is further arranged to detect substantially only light which has been focused to the measurement location and reflected by an interface of the eye.

14. The apparatus of claim 11, wherein the light has a single wavelength.

15. The apparatus of claim 11, wherein the light comprises two or more wavelengths.

16. The apparatus of claim 11, further comprising means to display a reference image, or object, for focusing by the eye during scanning, such that the eye may be repeatably aligned.

17. A micro-electromechanical system, comprising the apparatus of claim 11.

18. A hand-held device, comprising the micro-electromechanical system of claim 17.

19. A hand-held device, comprising the apparatus of claim 11.

20. A method of measuring changes in a property of an eye, comprising the steps of:
  a) directing light from a light source to a first reference location;
  b) spatially filtering light not received at the first reference location;
  c) receiving light from the first reference location and focusing the light to a measurement location;
  d) scanning the measurement location along a measurement line within the eye;
  e) receiving reflected light from the measurement location and focusing the reflected light to a second reference location;
  f) spatially filtering reflected light not received at the second reference location;
  g) measuring an intensity of the reflected light received at the second reference location;
  and using a processor:
  h) relating an intensity measurement to an apparent position of the measurement location;
  i) selecting intensity measurements of interest, the intensity measurements of interest representing measurement locations of interest; and
  j) deriving a distance between the measurement locations of interest, the distance being an apparent depth of the anterior chamber, the anterior chamber being defined by a first interface between the cornea and the aqueous humor of the eye and a second interface between the aqueous humor and the ocular lens of the eye, the method further comprising the steps of:
  k) comparing the derived apparent depth with a previous reference measurement of the apparent depth, so as to determine a change in the refractive index of the aqueous humor; and
  l) calculating a measure of change in concentration of an analyte of interest in the aqueous humor from the determined change of refractive index.

21. The method of claim 20, wherein the first and second reference locations are coincident.

22. The method of claim 20, wherein scanning step (d) is achieved by one of translating a lens; translating a lens and varying a numerical aperture (NA) of the lens; translating a mirror of a mirror assembly; varying a refractive index of a variable refractive index element; or varying a focal length of a variable focal length lens.

23. The method of claim 20, further comprising controlling the light such that the light has one of a static, jittered, swept or stepped wavelength.

24. The method of claim 20, further comprising the steps of modulating the light and detecting the phase of the light received at the second reference location.

25. The method of claim 20, further comprising the step of generating light having two or more wavelengths, such that two or more properties of the eye may be measured.

26. The method of claim 20, further comprising the step of producing light having two or more polarization states, such that two or more properties of the eye may be measured.

27. The method of claim 20, further comprising the steps of:
  i) producing a beam of coherent light;
  ii) splitting the light beam into a probe beam and a reference beam, such that the probe beam is controlled according to the method of any one of claims 20 to 29;
  iii) interfering the probe beam and the reference beam at a detector; and
  iv) measuring a resulting interference pattern.

28. The method of claim 20, further comprising the step of effecting a reference accommodation of the eye by placing a reference object in a line of sight of the eye.

29. An apparatus for measuring changes in a property of an eye, the property being an apparent depth of the anterior chamber defined by a first interface between the cornea and the aqueous humor of the eye and a second interface between the aqueous humor and the ocular lens of the eye, the apparatus comprising:
  a light source;
  a source optical element, adapted to direct light from the light source to a first reference location;
  an objective optical element, adapted to receive light from the first reference location and to focus the light to a measurement location, the objective optical element being further adapted to scan the measurement location along a measurement line within the eye and through the anterior chamber;
  a return optical element, adapted to receive reflected light from the measurement location and to focus the reflected light to a second reference location;
  an optical detector, adapted to measure an intensity of the reflected light received at the second reference location; and
  a processor, adapted to:
  i) relate intensity measurements of interest to apparent positions of the measurement location, so as to derive the apparent depth of the anterior chamber;
  ii) compare the derived apparent depth with a previous reference measurement of the apparent depth, so as to determine a change in the refractive index of the aqueous humor; and
  iii) calculate a measure of change in concentration of an analyte of interest in the aqueous humor from the determined change of refractive index.

30. The apparatus of claim 29, wherein the source optical element comprises one of a lens configuration, an optical fibre, or another light guide structure.

31. The apparatus of claim 29, wherein the first reference location is provided by one of a pinhole aperture, a source-detector combination, an optical fibre, or another light guide structure.

32. The apparatus of claim 29, wherein the objective optical element and/or the return optical element comprises a compound lens.

33. The apparatus of claim 32, further comprising a translation stage, adapted to translate a lens of the compound lens and thereby to scan the measurement location along the measurement line.

34. The apparatus of claim 29, wherein the objective optical element and the return optical element are constituted by the same optical element.

35. The apparatus of claim 34, wherein the first and second reference locations are coincident.

36. The apparatus of claim 29, wherein the light source comprises a white light source and one of a spectrometer, an etalon, or a multiplexer.

37. The apparatus of claim 29, further comprising a reference object for viewing by the eye, the reference object being positioned such that an accommodation of the eye may be repeatably achieved.

38. A micro-electromechanical system, comprising the apparatus of claim 29.

39. A hand-held device, comprising the micro-electromechanical system of claim 38.

40. A hand-held device, comprising the apparatus of claim 29.

* * * * *